United States Patent [19]

Nishihira et al.

[11] Patent Number: 5,162,563
[45] Date of Patent: Nov. 10, 1992

[54] PROCESS FOR PREPARING A DIESTER OF CARBOXYLIC ACID

[75] Inventors: Keigo Nishihira; Katsuhiko Mizutare; Shuji Tanaka, all of Ube, Japan

[73] Assignee: Ube Industries, Ltd., Ube, Japan

[21] Appl. No.: 599,134

[22] Filed: Oct. 17, 1990

[30] Foreign Application Priority Data

Oct. 24, 1989 [JP] Japan .................................. 1-274816
Jul. 31, 1990 [JP] Japan .................................. 2-201146

[51] Int. Cl.⁵ ............................................. C07C 69/96
[52] U.S. Cl. .................................. 558/260; 558/275; 558/277
[58] Field of Search .................... 558/277, 275, 260

[56] References Cited

FOREIGN PATENT DOCUMENTS 60-75447  4/1985 Japan .................................. 558/277
60-94943  5/1985 Japan .................................. 558/277

OTHER PUBLICATIONS

"Research of a New Method of Synthesis of Dimethyl Carbonate" (Jiang Xuan-Zhen et al., *Journal of Catalyst of China*, vol. 10, No. 1, Mar. 1989) and an English translation thereof.

*Primary Examiner*—Jose G. Dees
*Assistant Examiner*—Joseph M. Conrad, III
*Attorney, Agent, or Firm*—Frishauf, Holtz, Goodman & Woodward

[57] ABSTRACT

A process for preparing a diester of carbonic acid which comprises bringing carbon monoxide into contact with an ester of nitrous acid in a vapor phase at a pressure greater than atmospheric pressure in the presence of a solid catalyst having (a) a platinum group metal or a compound thereof and (b) at least one metal compound of a metal selected from the group consisting of iron, copper, bismuth, cobalt, nickel and tin; carried on a carrier.

24 Claims, No Drawings

PROCESS FOR PREPARING A DIESTER OF CARBOXYLIC ACID

BACKGROUND OF THE INVENTION

This invention relates to a process for preparing a diester of carboxylic acid. More particularly, it relates to a process for preparing a diester of carbonic acid which comprises bringing carbon monoxide into contact with an ester of nitrous acid selectively.

A diester of carbonic acid is an extremely available compound as an organic synthesis starting material for medicine and herbicides and also as an intermediate for preparation of a polycarbonate or urethane.

As a process for preparing a diester of carbonic acid, there have been practiced a method of reacting phosgene and an alcohol from extremely old times, but phosgene has extremely high toxicity and hydrochloric acid is a by-produced by the reaction of phosgene and an alcohol so that great care must be taken for a material to be used in an apparatus. Thus, it has been desired to develop a method using no phosgene.

Accordingly, a method for synthesizing a diester of carbonic acid from an alcohol and carbon monoxide has been researched various fields as a process of using no phosgene, and has been proposed (for example, Japanese Provisional Patent publications No. 75447/1985, No. 72650/1988 and No. 38010/1988, and WO-87/7601). These are methods in which a diester of carbonic acid is synthesized by oxygen oxidation reaction of an alcohol and carbon monoxide using copper halide or palladium halide as a catalyst, but involve the problems that a selectivity of a diester of carbonic acid based on carbon monoxide is low since carbon dioxide is by-produced and purification of a diester of carbonic acid is complicated due to formation of water.

Thus, as a method for improving the conventional ones, it has been proposed, in Japanese Provisional Patent Publication No. 181051/1985, a method of preparing a diester of carbonic acid which comprises reacting a nitrite and carbon monoxide in a vapor phase in the presence of a solid catalyst in which a platinum group metal or a compound thereof is carried on a carrier, and an oxidizing agent with an amount of 10 mole % or more as $O_2$ per carbon monoxide.

However, nevertheless an oxidizing agent such as oxygen co-exists with such a ratio to carbon monoxide in order to prevent by-production of a diester of oxalic acid, a significant amount of a diester of oxalic acid is by-produced so that a selectivity of a diester of carbonic acid is low and also the reaction rate is not sufficient. Also, a used range of a nitrite in "a mixed gas comprising a nitrite, carbon monoxide, an alcohol and oxygen" exceeds an explosion limit which is a problem in safety whereby the method is not an industrially sufficient one.

The process for preparing a diester of carbonic acid using a nitrite conventionally known is insufficient in reaction rate between carbon monoxide and a nitrite as mentioned above, and also a selectivity of a diester of carbonic acid is low so that there is a defect that a purification processing of the diester of carbonic acid formed becomes complicated. Further, the concentration range of nitrite in the reaction system exceeds an explosion limit so that there is a problem of accompanying danger in operations.

SUMMARY OF THE INVENTION

An object of the present invention is to provide an industrially suitable process for preparing a diester of carbonic acid which can produce a diester of carbonic acid under gentle reaction conditions with high selectivity and high yield.

Another object of the present invention is to provide a process for preparing a diester of carbonic acid with high selectivity and high yield while maintaining an activity of the solid catalyst for a long period of time.

The present inventors have carried out intensive investigations concerning a catalyst and the like when preparing a diester of carbonic acid by the vapor phase contact reaction of carbon monoxide and an ester of nitrous acid in the synthetic reaction of a diester of carbonic acid using a nitrite in order to overcome the problems in the conventional preparing process of a diester of carbonic acid as mentioned above, and consequently found that a diester of carbonic acid which is the title compound can be obtained when using a solid catalyst as mentioned below under gentle or mild reaction conditions whereby accomplishing the present invention.

That is, the present invention is a process for preparing a diester of carbonic acid which comprises bringing carbon monoxide into contact with an ester of nitrous acid in a vapor phase in the presence of a solid catalyst having (a) a platinum group metal or a compound thereof and
(b) at least one compound of a metal selected from the group consisting of iron, copper, bismuth, cobalt, nickel and tin carried on a carrier.

As one of the preferred embodiment of the present invention, said solid catalyst comprises having (a) a chloride of a platinum group metal and
(b) at least one compound of a metal selected from the group consisting of iron, copper, bismuth, cobalt, nickel and tin carried on a carrier.

As another embodiment of the present invention, said vapor phase reaction is carried out in the presence of a minute amount of hydrogen chloride.

DESCRIPTION OF THE PREFERRED EMBODIMENTS

In the following, the present invention is to be described in more detail.

As an ester of nitrous acid to be used in the present invention, there may be suitably mentioned an ester of nitrous of a lower aliphatic monohydric alcohol having 1 to 4 carbon atoms such as methyl nitrite, ethyl nitrite, n- (or iso)propyl nitrite, n- (or iso)butyl nitrite and sec-butyl nitrite; an ester of nitrous acid and an alicyclic alcohol such as cyclohexyl nitrite; an ester of nitrous acid and an aralkyl alcohol such as benzyl nitrite and phenylethyl nitrite; and the like, but preferably an ester of nitrous acid and a lower aliphatic monohydric alcohol having 1 to 4 carbon atoms, particularly preferably methyl nitrite and ethyl nitrite.

Also, the solid catalyst to be used in the present invention is one that carries (a) a platinum group catalyst such as palladium, platinum, iridium, ruthenium and rhodium or a compound of said metals, and (b) at least one compound of a metal selected from the group consisting of iron, copper, bismuth, cobalt, nickel and tin, carried on a carrier, more preferably one that carries (a) a compound of the above platinum group metal and (b)

at least one compound selected from the group consisting of iron, copper, bismuth, cobalt, nickel and tin, carried on a carrier. Further preferably one, that carries (a) a chloride of the above platinum group metal and (b) at least one compound selected from the group consisting of iron, copper, bismuth, cobalt, nickel and tin, carried on a carrier.

As the chloride of the platinum group metal, there may be specifically mentioned palladium chloride, platinum chloride, iridium chloride, ruthenium chloride and rhodium chloride, particularly preferably a chloride of palladium, ruthenium or rhodium, most preferably palladium chloride.

Of course, the "chloride of the platinum group metal" in the present invention is not limited to those as mentioned above, but it may be "a platinum group metal or a compound thereof as mentioned above" which is capable of forming a complex in which the above chloride or chlorine participate the reaction preferably under the presence of hydrogen chloride.

Such a compound of the platinum group metal may include halides such as bromide, iodide and fluoride, nitrates, sulfates, phosphates, acetates, oxalates and benzoates of said metals. More specifically, there may b mentioned, for example, palladium bromide, palladium iodide, palladium fluoride, palladium nitrate, palladium sulfate, palladium phosphate, palladium acetate, palladium oxalate, palladium benzoate, ruthenium iodide, rhodium bromide, rhodium iodide, rhodium nitrate, rhodium sulfate and rhodium acetate.

Of these, a halide of palladium, ruthenium or rhodium is particularly preferred, and palladium chloride is most preferred.

As the above compound of a metal selected from the group consisting of iron, copper, bismuth, cobalt, nickel and tin, there may be suitably mentioned, for example, halides such as chloride, bromide, iodide and fluoride, nitrates, sulfates, phosphates and acetates of said metals, and of these, halides of said metals are particularly suitable.

As a carrier to be carried with the platinum group metal or a compound thereof, and at least one of the compound of metal selected from the group consisting of iron, copper, bismuth, cobalt, nickel and tin, there may be suitably mentioned, for example, diatomaceous earth, activated charcoal, silicon carbide, titania and alumina, and activated charcoal is particularly preferred.

A method of carrying the aforesaid platinum group metal or a compound thereof including a chloride thereof, and the compound of metals such as iron, copper, bismuth, cobalt, nickel and tin on the carrier need not be a specific one but it may be carried out by the conventionally practiced method such as the impregnating method (dipping adsorption method), the kneading method, the precipitation deposition method and the co-precipitation method, but in the present invention, it is desired to prepare the catalyst by the impregnating method or the kneading method.

A carried amount of the above platinum group metal or a compound thereof to be carried on a carrier is generally 0.1 to 10% by weight, particularly preferably 0.5 to 2% by weight in terms of a metal of the platinum group metal.

Also, a carried amount of the compound of the metal such as iron, copper, bismuth, cobalt, nickel and tin to be carried on a carrier is generally 1 to 50 gram atomic equivalents, preferably 1 to 10 gram atomic equivalents in terms of an amount of these metals.

Also, in the present invention, the above catalyst can be used in the form of a powder or granule, and a particle size thereof is not particularly limited, but it is preferred to use powder having 20 to 100 $\mu$m generally employed and granule with 4 to 200 mesh generally employed.

In the present invention, as described above, a particularly characteristic matter is to use a solid catalyst carried on a carrier, in addition to the platinum group metal or a compound thereof (first component), at least one compound of a metal selected from the group consisting of iron, copper, bismuth, cobalt, nickel and tin (second component). That is, in the present invention, these compounds of a metal (second component) act as a role of a cocatalyst. By carrying these metal compounds on a carrier with an amount as mentioned above, the reaction rate of carbon monoxide and an ester of nitrous acid is remarkably improved and the deactivating rate of the catalyst is also delayed as compared with the case where the platinum group metal or a compound thereof alone is carried thereon.

However, in order to further improve the lifetime of the catalyst activity, it is more preferred to carry out the contact reaction of carbon monoxide and an ester of nitrous acid in the presence of a solid catalyst having (1) a chloride of platinum group metal and
(2) at least one compound of a metal selected from the group consisting of iron, copper, bismuth, cobalt, nickel and tin carried on a carrier, and more preferably, under the co-presence of a minute amount of hydrogen chloride, whereby a gradual decrease in catalyst activity due to the dissipation of a minute amount of a chlorine component from the catalyst during the reaction can be prevented and the reaction can be carried out by maintaining the catalyst activity at a high degree for a long period of time.

Hydrogen chloride to be used in the present invention is preferably anhydrous.

The method of co-presenting hydrogen chloride in the above, reaction system of carbon monoxide and an ester of nitrous acid is not particularly limited, but for example, as described in detail below, preferred methods are the method in which a minute amount of hydrogen chloride is added continuously, and the method in which using a moving bed system reactor, a part of the catalyst is continuously taken out from the filling bed to contact with hydrogen chloride and returned to the reactor. More specifically, it is preferred to select a suitable method-based on the "above reaction system of carbon monoxide and an ester of nitrous acid" employed from the "reaction system" which can be practically applied in the present invention as mentioned below.

First, the method in which a minute mount of hydrogen chloride is added in the reaction system continuously is to be explained. An amount of hydrogen chloride is desirably 1 to 50 mole %, more preferably 5 to 20 mole % per unit time based on the platinum metal in the catalyst. This amount corresponds to a chlorine content dissipated from the catalyst during the above reaction of carbon monoxide and an ester of nitrous acid. If the amount is larger than the above range, the above reaction is inhibited due to excess adsorption of hydrogen chloride to the catalyst. If it is specifically mentioned by referring to the actual reaction example, for example, when the starting materials are reacted in a fixed bed reactor with a gas space velocity (GHSV) of 3000 hr$^{-1}$, it is preferred to add 10 to 500 volume ppm, more preferably 20 to 100 volume ppm of hydrogen chloride to a feed gas and supply it to the catalyst bed continuously to supplement the chlorine content dissipated from the catalyst.

Next, the method where the reaction is carried out at the moving bed system is a method in which, as described above, hydrogen chloride gas is contacted with and adsorbed to the catalyst taken out from the catalyst filling bed in the reactor to supplement the chlorine dissipated content, and then the catalyst is returned in the reactor. The method of adsorbing hydrogen chloride to the catalyst taken out may be a method generally considered, and for example, it may be carried out by filling the catalyst taken out in a suitable vessel and then passing hydrogen chloride gas diluted with nitrogen therethrough under gentle conditions. In this case, a concentration of hydrogen chloride, 0.1 to 10% by volume is suitable in view of operation, but it is not limited by the above range, and it may be 100% by volume without problem. Also, since hydrogen chloride is rapidly adsorbed to the catalyst, a time of contacting hydrogen chloride with the above "taken out catalyst" is sufficient with 1 to 30 minutes, which may vary depending on the space velocity (SV) during the contact operation. This contact operation is preferably carried out under normal temperature and normal pressure, but these ranges are not limited, and for example, it can be sufficiently carried out at a temperature of 0° to 200° C. and a pressure of $-0.5$ to 5 kg/cm$^2$G.

Further, it is one of the characteristic features of the present invention that the contact reaction of carbon monoxide and an ester of nitrous acid can be carried out under extremely gentle conditions. For example, the reaction can be carried out at a temperature of 0° to 200° C., preferably 50° to 120° C. under normal pressure. Of course, it can be carried out under pressurized system and can be carried out at a pressure of 1 to 20 kg/cm$^2$G and a temperature of 50° to 150° C.

In the present invention, the aforesaid starting material nitrite can be easily synthesized by, for example, generating a mixed gas of nitrogen monoxide (NO) and nitrogen dioxide (NO$_2$) by nitric acid or sulfuric acid decomposition of an aqueous sodium nitrite, then making nitrogen dioxide (NO$_2$) by oxidizing part of NO in the mixed gas with molecular oxygen to obtain NO$_x$ gas with NO/NO$_2$=1/1 (volume ratio), and then contacting an alcohol thereto. When considering the synthesis of an ester of nitrous acid, it is particularly preferred that the above contact reaction of carbon monoxide and an ester of nitrous acid is carried out under a slightly pressured condition of 2 to 3 kg/cm$^2$G or so.

The above reaction system of carbon monoxide and an ester of nitrous acid may be carried out either the batch system or the continuous system in the vapor phase, but the continuous system is industrially more advantageous. Also, as the existing form of the catalyst in the system, the reaction may be carried out by using either of fixed bed, moving bed or fluidized bed reactor.

In the present invention, it is desired to feed carbon monoxide and an ester of nitrous acid as the starting gases by diluting with an inert gas such as nitrogen gas to the aforesaid reactor, and the composition thereof is not particularly limited from the view point of the reaction. However, from the view point of safety, a concentration of the above an ester of nitrous acid is preferably 20% by volume or less, more preferably 5 to 20% by volume. Accompanying this, a concentration of carbon monoxide is preferably in the range of 5 to 20% by volume from economical viewpoint. That is, considering an industrial production process, it is preferred to circulate gases such as carbon monoxide and an ester of nitrous acid to be supplied to the reaction system, and purge part of said circulating gas out of the system. Also, from the fact that a conversion of carbon monoxide per one pass is 20 to 30%, even when the concentration of carbon monoxide is heightened than 20% by volume, no merit can be obtained and loss is increased, while it is made lower than 5% by volume, productivity is lowered. However, when ignoring the economic problem, the concentration of carbon monoxide can be made by 80% by volume. That is, the ester of nitrous acid may be fed by diluting with carbon monoxide instead of the above inert gas.

Accordingly, a used ratio of carbon monoxide and a nitrite is preferably in the range of 0.1 to 10 mole, more preferably 0.25 to 1 mole of carbon monoxide per mole of the nitrite.

In the present invention, a space velocity of a gas containing carbon monoxide and ester of nitrous acid to be fed in the above reactor is preferably in the range of 500 to 20000 hr$^{-1}$, more preferably 2000 to 5000 hr$^{-1}$.

Further, in the process of the present invention, the aforesaid nitrite decomposes to produce ester of nitrous acid monoxide (NO) after participating the reaction. It is preferred that the NO is recovered from a reaction gas led out from the above reactor, reacted with oxygen and an alcohol corresponding to the above ester of nitrous acid to convert it into an ester of nitrous acid again and circulated.

Thus, a reaction gas containing, in addition to a diester of carbonic acid which is the title product, a by-product such as a diester of oxalic acid, unreacted carbon monoxide and an ester of nitrous acid, nitrogen monoxide, carbon dioxide and an inert gas is led out from the reactor, and after cooling the reaction gas, uncondensed gases such as carbon monoxide, an ester of nitrous acid, nitrogen monoxide, carbon dioxide and an inert gas are circulated again in the reactor while purging part thereof, and a diester of carbonic acid is separated and purified from a condensate by the conventional method such as distillation.

An ester of nitrous acid of the starting material can be generally prepared by reacting an alcohol and a nitrogen oxide in the presence of molecular oxygen, if necessary, as mentioned above, and unreacted alcohol and nitrogen oxide (particularly nitrogen monoxide), and a minute amount of water and oxygen depending on the cases, are contained in the prepared gas in addition to the ester of nitrous acid. In the present invention, even when such an ester of nitrous acid-containing gas is used as a source for the ester of nitrous acid, good results can be obtained.

In the present invention, by carrying out the treatments as mentioned above, lowering the activity of the catalyst in the conventional method can be prevented and production of a diester of carbonic acid by the reaction of carbon monoxide and an ester of nitrous acid can be continued with high yield and high selectivity, and also with stable conditions for a long period of time.

EXAMPLES

In the following, the process of the present invention will be explained specifically by referring to Examples and Comparative examples, but the present invention is not limited by these.

A space time yield (STY) Y (g/l·hr) in each Example and Comparative example is calculated from the following equation:

$$Y = a/(b \times \theta)$$

wherein $\theta$ (hr) is a contact reaction time of carbon monoxide and a nitrite, a (g) is an amount of a diester of carboxylic acid and b (l) is a filled amount of the catalyst to the reactor.

Also, a selectivity X (%) in each Example and Comparative example is calculated by using carbon monoxide to be supplied as standard, and obtained from the following formula by making amounts of a diester of carbonic acid, a diester of oxalic acid and carbon dioxide formed by the above $\theta$ (hr) as c (mole), d (mole) and e (mole), respectively.

$$X = \{c/(c + 2 \times d + e)\} \times 100$$

EXAMPLE 1

Preparation of a catalyst

In 100 ml of 5N hydrochloric acid were dissolved 0.35 g of palladium chloride and 0.34 g of cupric chloride (dihydrate), and after dipping 10 g of granular activated charcoal therein, the mixture was filtered and the filtrate was washed with water and dried at 100° C. to prepare a catalyst (PdCl$_2$—CuCl$_2$/C) carried palladium chloride and cupric chloride on the activated charcoal.

Preparation of a diester of carbonic acid

The above catalyst (7 ml) was filled in a vapor phase reactor (attached with an outer jacket) having an inner diameter of 20 mm, and then the reactor was fixed vertically and a heating medium was circulated in the jacket of the reactor to control a temperature in a catalyst bed to 100° C.

From the upper end of the reactor, a mixed gas comprising a gas containing methyl nitrite synthesized from nitrogen monoxide, oxygen and methanol, and carbon monoxide, i.e. a mixed gas comprising a composition of 15% by volume of methyl nitrite, 10% by volume of carbon monoxide, 3% by volume of nitrogen monoxide, 6% by volume of methanol and 66% by volume of nitrogen was supplied with a space velocity (GHSV) of 3000 hr$^{-1}$ to subject the reaction under normal pressure.

Then, the reaction product passed through the reactor was captured by passing through an ice-cold methanol.

The captured solution thus obtained was analyzed by gas chromatography to give the results that dimethyl carbonate was formed with STY of 220 g/l·hr and a selectivity of 96%. Also, dimethyl oxalate and methyl formate were confirmed to be present as by-products.

COMPARATIVE EXAMPLE 1

Preparation of a catalyst

In 100 ml of 5N hydrochloric acid was dissolved 0.35 g of palladium chloride, and after dipping 10 g of granular activated charcoal therein, the mixture was filtered and the filtrate was washed with water and dried at 100° C. to prepare a catalyst (PdCl$_2$/C) carried palladium chloride alone on the activated charcoal.

Preparation of a diester of carbonic acid

Dimethyl carbonate was prepared in the same manner as in Example 1 except for using the above catalyst.

The captured solution thus obtained was analyzed by gas chromatography to give the results that dimethyl carbonate was formed with STY of 120 g/l·hr and a selectivity of 90%.

COMPARATIVE EXAMPLE 2

Preparation of a diester of carbonic acid

Dimethyl carbonate was prepared by carrying out the reaction of carbon monoxide and methyl nitrite in the same manner as in Example 1 except that the catalyst prepared in Comparative example 1 was used, and a composition of a mixed gas supplied from the upper end of the reactor was 15% by volume of methyl nitrite, 10% by volume of carbon monoxide, 2% by volume of oxygen, 6% by volume of methanol and 67% by volume of nitrogen.

The captured solution thus obtained was analyzed by gas chromatography to give the results that dimethyl carbonate was formed with STY of 90 g/l·hr and a selectivity of 72%.

EXAMPLES 2 TO 8

Preparation of a catalyst

In each Example, "a catalyst having a platinum group metal compound and at least one compound of a metal selected from iron, copper and bismuth carried thereon" shown in Table 1 was prepared in accordance with the method in Example 1.

Carried amounts of the platinum group metal compound in these catalysts are all 1% by weight as a platinum group metal based on the carrier.

Preparation of a diester of carbonic acid

In each Example, dimethyl carbonate in Examples 2 to 7 and diethyl carbonate in Example 8 were prepared in the same manner as in Example 1 except that the above catalysts were used, and in Example 8, a mixed gas of a gas containing ethyl nitrite synthesized from nitrogen monoxide, oxygen and ethanol, i.e. a composition of a mixed gas of 15% by volume of ethyl nitrite, 10% by volume of carbon monoxide, 3% by volume of nitrogen monoxide, 6% by volume of methanol and 66% by volume of nitrogen was supplied from the upper end of the reactor. The results are shown in Table 1.

TABLE 1

| Example No. | Kind of catalyst | Name of title diester of carboxylic acid formed | Selectivity of title diester of carboxylic acid (%) | STY of title diester of carboxylic acid (g/l hr) |
|---|---|---|---|---|
| 2 | PdCl$_2$—BiCl$_3$/C | dimethyl carbonate | 93 | 280 |
| 3 | PdCl$_2$—Fe$_2$Cl$_3$/C | dimethyl carbonate | 92 | 260 |

TABLE 1-continued

| Example No. | Kind of catalyst | Name of title diester of carboxylic acid formed | Selectivity of title diester of carboxylic acid (%) | STY of title diester of carboxylic acid (g/l hr) |
|---|---|---|---|---|
| 4 | $RuCl_3$—$CuCl_2$/C | dimethyl carbonate | 93 | 130 |
| 5 | $RhCl_3$—$CuCl_2$/C | dimethyl carbonate | 92 | 120 |
| 6 | $PdCl_2$—$BiCl_3$—$Fe_2Cl_3$/C | dimethyl carbonate | 94 | 350 |
| 7 | $PdBr_2$—$Fe_2Br_3$/C | dimethyl carbonate | 88 | 170 |
| 8 | $PdCl_2$—$BiCl_3$/C | diethyl carbonate | 94 | 350 |

Remarks:
(1) "$PdCl_2$—$BiCl_3$/C" at the column of "Kind of catalyst" in Example 2 shows a catalyst with carried $PdCl_2$ and $BiCl_3$ on granular activated charcoal, which is the same as in Examples 3 to 8.
(2) In Examples 2 to 8, the metal compound of the second component (and third component) is carried with equal amounts in gram atomic eqivalent in terms of a metal amount based on a platinum group metal in the compound of platinum group metal.

EXAMPLE 9

After filling 7 ml of a catalyst ($PdCl_2$-$BiCl_3$/C) in which $PdCl_2$ and $BiCl_3$ were carried on a granular activated charcoal in a vapor phase reactor (attached with an outer jacket) having an inner diameter of 20 mm, and then the reactor was fixed vertically and a heating medium was circulated in the jacket of the reactor to control a temperature in a catalyst bed to 100° C.

From the upper end of the reactor, a mixed gas comprising a gas containing methyl nitrite synthesized from nitrogen monoxide, oxygen and methanol, and carbon monoxide, i.e. a mixed gas comprising a composition of 15% by volume of methyl nitrite, 10% by volume of carbon monoxide, 3% by volume of nitrogen monoxide, 6% by volume of methanol, 100 ppm by volume of hydrogen chloride and 66% by volume of nitrogen was supplied with a space velocity (GHSV) of 3000 $hr^{-1}$ to subject the reaction under normal pressure.

Then, the reaction product passed through the reactor was captured by passing through an ice-cold methanol. The captured solution thus obtained was analyzed by gas chromatography.

As the results, while the STY of dimethyl carbonate was 500 g/l·hr at an initial stage, it was lowered to 350 g/l·hr at after 10 hours. However, it was not changed as 350 g/l·hr by 100 hours from the initiation of the reaction, which was the completion of the reaction. Also, a selectivity of dimethyl carbonate based on carbon monoxide was 97% at an initial stage and it was lowered to 92% at after 10 hours from the initiation of the reaction by increase of dimethyl oxalate which is a by-product, but it was substantially the same by the completion of the reaction (100 hours after initiation of the reaction).

EXAMPLE 10

A catalyst (200 ml) which is the same used in Example 9 was filled in a vapor phase reactor (attached with a taken out tube at the bottom portion of a catalyst bed) having an inner diameter of 40 mm. The same type catalyst regenerating tube was separately prepared and 200 ml of the same catalyst was filled therein.

Then, the vapor phase reactor and the catalyst regenerating tube were fixed vertically, and to the vapor phase reactor was supplied from the upper end a mixed gas comprising a gas containing methyl nitrite synthesized from nitrogen monoxide, oxygen and methanol, and carbon monoxide, i.e. a mixed gas comprising a composition of 15% by volume of methyl nitrite, 10% by volume of carbon monoxide, 3% by volume of nitrogen monoxide, 6% by volume of methanol and 66% by volume of nitrogen was supplied with a space velocity (GHSV) of 3000 $hr^{-1}$ to subject the reaction under normal pressure.

From one hour after initiation of the reaction, the catalyst was taken out from the bottom portion of the catalyst bed of the reactor through the taken out tube at the bottom of the catalyst bed with a ratio of 10 ml per one hour, and it was supplied to the upper portion of the catalyst regenerating tube and simultaneously a catalyst was taken out from the bottom portion of the catalyst regenerating tube through the taken out tube at the bottom of the catalyst bed of said catalyst regenerating tube with a ratio of 20 ml per one hour and supplied to the upper portion of the reactor. And to the catalyst regenerating tube was passed nitrogen gas containing 100 ppm by volume of hydrogen chloride therethrough from one hour after initiation of the reaction with a space velocity of 500 $hr^{-1}$.

As described above, a gas flown out from the reactor after carrying out the reaction of methyl nitrite and carbon monoxide was captured through an ice-cold methanol and subjected to quantitative determination by gas chromatography.

Under the above conditions, the reaction was carried out for 100 hours continuously and sampling of the reaction product and analysis by gas chromatography were carried out every 5 hours as described above.

As the results, STY of dimethyl carbonate was 500 g/l·hr at an initial stage, it was lowered to 370 g/l·hr at after 10 hours from initiation of the reaction. However, it was not changed as 350 to 370 g/l·hr by 100 hours from the initiation of the reaction, which was the completion of the reaction. Also, a selectivity of dimethyl carbonate based on carbon monoxide was 97% at an initial stage and it was lowered to 93% at after 10 hours from the initiation of the reaction by an increase of dimethyl oxalate which is a by-product, but it became constant as 90 to 93% by the completion of the reaction (100 hours after initiation of the reaction).

The process of the present invention is, as described above, to provide a process which can prepare a diester of carbonic acid with high selectivity and high yield under gentle conditions without accompanying any dangerous operation by reacting carbon monoxide and an ester of nitrous acid in the presence of a solid catalyst having a platinum group metal or a compound thereof and at least one compound of a metal selected from the group consisting of iron, copper, bismuth, cobalt, nickel and tin as a second component carried on a carrier under conditions of low temperature and low pressure and subjecting it to a vapor phase reaction, whereas the conventional process of a diester of carbonic acid by a vapor phase contact reaction of carbon monoxide and a nitrite involves the defects that the reaction rate is not sufficient, the selectivity of the diester of carbonic acid is low and separating and purifying operations of the diester of carboxylic acid from the reaction product becomes complicated, and also involves the problem that a dangerous operation is involved since the concentration range of the nitrite used exceeds explosion limit.

Also, as compared with the conventionally known liquid phase process, the process of the present invention can be carried out in a vapor phase so that it is not necessary to separate the catalyst from the reaction mixture and no dissolution of metal component from the catalyst whereby separation and purification of the diester of carbonic acid from the reaction mixture is easy, and thus, the process of the present invention has an effect of having high superiority in production of an industrial scale.

Further, by incorporating a minute amount of hydrogen chloride in the reaction system and using a chloride of a platinum group metal as the first component of the catalyst, the lifetime of the catalyst can be remarkably stably elongated.

We claim:

1. A process for preparing a diester of carbonic acid which comprises contacting carbon monoxide with an ester of nitrous acid in a vapor phase at a pressure of 1 to 20 kg/cm$^2$G in the presence of a solid catalyst comprising
   (a) a platinum group metal or a compound thereof; and
   (b) at least one metal compound of a metal selected from the group consisting of iron, copper, bismuth, cobalt, nickel and tin; carried on a carrier.

2. The process according to claim 1, wherein said ester of nitrous acid is selected from the group consisting of an ester of nitrous acid and a lower aliphatic monohydric alcohol having 1 to 4 carbon atoms, an ester of nitrous acid and an alicyclic alcohol and an ester of nitrous acid and an aralkyl alcohol.

3. The process according to claim 2, wherein said ester of nitrous acid is selected from the group consisting of methyl nitrite, ethyl nitrite, n-propyl nitrite, isopropyl nitrite, n-butyl nitrite, isobutyl nitrite, sec-butyl nitrite, cyclohexyl nitrite, benzyl nitrite and phenylethyl nitrite.

4. The process according to claim 2, wherein said ester of nitrous acid is an ester of nitrous acid and a lower aliphatic monohydric alcohol having 1 to 4 carbon atoms.

5. The process according to claim 4, wherein said is ester of nitrous acid, is methyl nitrite or ethyl nitrite.

6. The process according to claim 1, wherein an amount of a catalyst component (a) to be carried on the carrier is 0.1 to 10% by weight in terms of a metal of the platinum group metal.

7. The process according to claim 6, wherein an amount of the catalyst component (a) is 0.5 to 2% by weight.

8. The process according to claim 1, wherein an amount of a catalyst component (b) to be carried on the carrier is 1 to 50 gram atomic equivalents in terms of an amount of the metal.

9. The process according to claim 8, wherein an amount of the catalyst component (b) is 1 to 10 gram atomic equivalents.

10. The process according to claim 1, wherein said compound of the platinum group metal is selected from the group consisting of halides, nitrates, sulfates, phosphates, acetates, oxalates and benzoates of said metals.

11. The process according to claim 10, wherein said compound of the platinum group metal is selected from the group consisting of palladium bromide, palladium iodide, palladium fluoride, palladium nitrate, palladium sulfate, palladium phosphate, palladium acetate, palladium oxalate, palladium benzoate, ruthenium iodide, rhodium bromide, rhodium iodide, rhodium nitrate, rhodium sulfate and rhodium acetate.

12. The process according to claim 1, wherein said compound of a platinum group metal is a chloride of the platinum group metal.

13. The process according to claim 12, wherein said chloride is selected from the group consisting of palladium chloride, platinum chloride, iridium chloride, ruthenium chloride and rhodium chloride.

14. The process according to claim 12, wherein the reaction is carried out in the presence of a minute amount of hydrogen chloride.

15. The process according to claim 14, wherein the amount of hydrogen chloride is 1 to 50 mole % per unit time based on the platinum metal in the catalyst.

16. The process according to claim 1, wherein the reaction is carried out at a temperature of 50° to 120° C.

17. The process according to claim 1, wherein the reaction is carried out at a temperature of 50° to 150° C. under a pressure of 1 to 20 kg/cm$^2$G.

18. The process according to claim 1, wherein the carbon monoxide and the ester of nitrous acid are fed in the vapor phase reaction system with a concentration of carbon monoxide of 5 to 20% by volume and a concentration of the ester of nitrous acid of 20% by volume or less.

19. The process according to claim 18, wherein a ratio of the carbon monoxide and the ester of nitrous acid is 0.1 to 10 mole of the carbon monoxide per mole of the ester of nitrous acid.

20. The process according to claim 18, wherein of a gas containing the carbon monoxide and the ester of nitrous acid is fed at a space velocity of 500 to 20,000 hr$^{-1}$.

21. The process according to claim 1, wherein (b) is a halide, nitrate, sulfate, phosphate or acetate of said metal.

22. The process according to claim 1, wherein the pressure is 2 to 3 kg/cm$^2$G.

23. The process according to claim 1, wherein the platinum group metal is selected from the group consisting of platinum, iridium, ruthenium and rhodium; the metal for (b) is selected from the group consisting of bismuth, cobalt, nickel and tin; and the ester of nitrous acid has 2 to 4 carbon atoms.

24. The process according to claim 6, wherein an amount of the catalyst component (b) to be carried on the carrier is 1 to 50 gram atomic equivalents in terms of an amount of the metal; the reaction is carried out at a temperature of 50° to 120° C. the carbon monoxide and the ester of nitrous acid are fed in a vapor phase reaction system with a concentration of carbon monoxide of 5 to 20% by volume or less and a concentration of the ester of nitrous acid of 20% by volume or less; the carbon monoxide and the ester of nitrous acid are in a ratio of 0.1 to 10 moles of carbon monoxide per mole of the nitrite; and a gas containing the carbon monoxide and the ester of nitrous acid is fed at a space velocity of 500 to 20,000 hr$^{-1}$.

* * * * *